(12) United States Patent
Oshinski et al.

(10) Patent No.: US 9,858,687 B2
(45) Date of Patent: Jan. 2, 2018

(54) SYSTEMS, METHODS, AND COMPUTER READABLE STORAGE MEDIA STORING INSTRUCTIONS FOR GENERATING AN IMAGE INTEGRATING FUNCTIONAL, PHYSIOLOGICAL AND ANATOMICAL IMAGES

(71) Applicants: EMORY UNIVERSITY, Atlanta, GA (US); GEORGIA TECH RESEARCH CORPORATION, Atlanta, GA (US)

(72) Inventors: John N. Oshinski, Decatur, GA (US); Jonathan D. Suever, Atlanta, GA (US); Michael S. Lloyd, Avondale Estates, GA (US); Angel R. Leon, Atlanta, GA (US)

(73) Assignees: Emory University, Atlanta, GA (US); Georgia Tech Research Corporation, Atlanta, GA (US)

( * ) Notice: Subject to any disclaimer, the term of this patent is extended or adjusted under 35 U.S.C. 154(b) by 90 days.

(21) Appl. No.: 13/742,648

(22) Filed: Jan. 16, 2013

(65) Prior Publication Data
US 2013/0182929 A1    Jul. 18, 2013

Related U.S. Application Data

(60) Provisional application No. 61/587,150, filed on Jan. 17, 2012.

(51) Int. Cl.
*G06T 11/00* (2006.01)
*G01R 33/563* (2006.01)
(Continued)

(52) U.S. Cl.
CPC ............ *G06T 11/005* (2013.01); *G06T 7/33* (2017.01); *A61B 5/04012* (2013.01);
(Continued)

(58) Field of Classification Search
CPC ..... A61B 5/0044; A61B 5/6852; A61B 19/50; A61B 2017/00243; A61B 6/503;
(Continued)

(56) References Cited

U.S. PATENT DOCUMENTS 6,978,184 B1  12/2005  Marcus et al.
7,343,196 B2   3/2008  Okerlund et al.
(Continued)

OTHER PUBLICATIONS

Bistoquet et al. "Myocardial deformation recovery from cine MRI using a nearly incompressible biventricular model." Medical Image Analysis, 2008; 12(1): 69-85.
(Continued)

*Primary Examiner* — Kenny Cese
(74) *Attorney, Agent, or Firm* — Emory Patent Group

(57) ABSTRACT

Systems, methods and computer-readable storage mediums relate to generating an image that includes functional, anatomical, and physiological images. The generated image may be an integrated image based on the functional image on which the anatomical and physiological images are mapped. The generated image may indicate more than one location of optimal lead placement. The generated image may be useful in pre-planning cardiac intervention procedures.

20 Claims, 5 Drawing Sheets

(51) Int. Cl.
*A61B 5/04* (2006.01)
*G06T 7/33* (2017.01)
*A61B 90/00* (2016.01)
*G06T 3/00* (2006.01)

(52) U.S. Cl.
CPC .. *A61B 2090/374* (2016.02); *G01R 33/56325* (2013.01); *G06T 3/0068* (2013.01); *G06T 2207/10072* (2013.01); *G06T 2207/10088* (2013.01); *G06T 2207/10096* (2013.01); *G06T 2207/20221* (2013.01); *G06T 2207/30048* (2013.01)

(58) Field of Classification Search
CPC ..... A61B 6/504; A61B 8/0883; A61B 8/0891; A61B 2090/374; A61B 5/04012; G06T 2207/30048; G06T 7/0081; G06T 2207/10088; G06T 11/005; G06T 2207/10096; G06T 2207/20221; G06T 3/0068; G01R 33/56325
USPC .................................................. 382/128, 131
See application file for complete search history.

(56) References Cited

U.S. PATENT DOCUMENTS

| | | | |
|---|---|---|---|
| 7,463,919 B2 * | 12/2008 | Hamilton | A61B 5/055 600/410 |
| 7,499,743 B2 | 3/2009 | Vass et al. | |
| 7,996,063 B2 | 8/2011 | Vass et al. | |
| 2004/0087850 A1 | 5/2004 | Okerlund et al. | |
| 2004/0153128 A1 * | 8/2004 | Suresh | G06F 19/3437 607/14 |
| 2007/0014452 A1 * | 1/2007 | Suresh | G06F 19/3437 382/128 |
| 2007/0055124 A1 | 3/2007 | Viswanathan et al. | |
| 2009/0254140 A1 * | 10/2009 | Rosenberg | A61B 5/0422 607/17 |
| 2009/0318995 A1 * | 12/2009 | Keel | A61B 5/11 607/17 |
| 2010/0074487 A1 * | 3/2010 | Miyamoto | A61B 6/503 382/128 |
| 2010/0266176 A1 * | 10/2010 | Masumoto | G06F 19/321 382/128 |
| 2010/0268059 A1 * | 10/2010 | Ryu | A61B 5/042 600/407 |
| 2010/0317962 A1 * | 12/2010 | Jenkins | A61B 5/055 600/411 |
| 2011/0071382 A1 * | 3/2011 | Miyazaki | A61B 5/0037 600/413 |
| 2011/0144510 A1 * | 6/2011 | Ryu | A61B 5/042 600/509 |
| 2011/0160792 A1 | 6/2011 | Fishel | |
| 2011/0313291 A1 * | 12/2011 | Chono | A61B 8/08 600/440 |
| 2012/0027276 A1 * | 2/2012 | Chono | A61B 5/02028 382/128 |
| 2012/0089016 A1 * | 4/2012 | Mizuno | G06T 11/206 600/425 |
| 2012/0116237 A1 * | 5/2012 | Harks | A61B 5/06 600/508 |

OTHER PUBLICATIONS

Delfino et al. "Cross-Correlation Delay to Quantify Myocardial Dyssynchrony From Phase Contrast Magnetic Resonance (PCMR) Velocity Data." Journal of Magnetic Resonance Imaging, 2008; 28(5): 1086-1091.
Delfino et al. "Determination of Transmural, Endocardial, and Epicardial Radial Strain and Strain Rate From Phase contrast MR Velocity Data." Journal of Magnetic Resonance Imaging, 2008; 27(3): 522-528.
Delfino et al. "Role of MRI in Patient Selection for CRT." Echocardiography, 2008; 25(10): 1176-1185.
Delfino et al. "Three-directional Myocardial Phase-Constrast Tissue Velocity MR Imaging with Navigator-Echo Gating: In Vivo and in Vitro Study." Radiology, 2008; 246(3):917-925.
Fielden et al. "A New Method for the Determination of Aortic Pulse Wave Velocity Using Cross-Correlation on 2D PCMR Velocity Data." Journal of Magnetic Resonance Imaging 2008; 27(6):1382-1387.
Fornwalt et al. "Cross-correlation Quantification of Dyssynchrony: A New Method for Quantifying the Synchrony of Contraction and Relaxation in the Heart." Journal of American Society of Echocardiography 2007; 20(12):1330-1337.
Fornwalt et al. "Quantification of Left Ventricular Internal Flow From Cardiac Magnetic Resonance Images in Patients with Dyssynchronous Heart Failure." Journal of Magnetic Resonance Imaging 2008; 28(2):375-381.
Fornwalt et al. "Effects of Region of Interest Tracking on the Diagnosis of Left Ventricular Dyssynchrony from Doppler Tissue Images." Journal of American Society of Echocardiography, 2008; 21(3):234-240.
Fornwalt et al. "Acute Pacing-Induced Dyssynchronous Activation of the Left Ventricle Creates Systolic Dyssynchrony with Preserved Diastolic Synchrony." Journal of Cardiovascular Eletrophysiology, 2008; 19(5):483-488.
Fornwalt et al. "It's Time for a Paradigm Shift in the Quantitative Evaluation of Left Ventricular Dyssynchrony." Journal of American Society of Echocardiography, 2009; 22(6):672-676.
Fornwalt et al. "Variability in Tissue Doppler Echocardiographic Measures of Dyssynchrony Is Reduced With Use of a Larger Region of Interest." Journal of American Society of Echocardiography, 2009; 22(5):478-785.
Fornwalt et al. "Agreement is Poor Amongst Current Criteria Used to Define Response to Cardiac Resynchronization Therapy." Circulation, 2010; 121(18):1985-1991.
Johnson et al. "Coronary artery flow measurement using navigator echo gated phase contrast magnetic resonance velocity mapping at 3.0T." Journal of Biomechanics, 2008; 41(3):595-602.
Khan et al. "Targeted Left Ventricular Lead Placement to Guide Cardiac Resynchronization Therapy." Journal of the American College of Cardiology, 2012; 59(17):1509-1518.
Ma et al. "Real-Time Cardiac MR Anatomy and Dyssynchrony Overlay for Guidance of Cardiac Resynchronization Therapy Procedures: Clinical Results Update." FIMH 2011, LNCS 6666, Springer-Verlage Berlin Heidelberg; pp. 313-314.
Ma et al. "An integrated platform for image-guided resynchronization therapy." Physics in Medicine and Biology, 2012; 57(10):2953-2968.
Morgan et al. "Lead positioning for cardiac resynchronization therapy: techniques and priorities." Eurospace, 2009; 11:v22-28.
Shetty et al. "152: Real-Time Cardiac MR Anatomy and Dyssynchrony Overlay to Guide Left Ventricular Lead Placement in CRT." Heart, 2001; 97(Suppl. 1):A84-A85.
Sun et al. "Automatic Plaque Characterization Employing Quantitative and Multicontrast MRI." Magnetic Resonance in Medicine, 2008; 59(1):174-180.
Tournoux et al. "Integrating functional and anatomical information to guide cardiac resynchronization therapy." European Journal of Heart Failure, 2010; 12:52-57.

\* cited by examiner

SYSTEMS, METHODS, AND COMPUTER READABLE STORAGE MEDIA STORING INSTRUCTIONS FOR GENERATING AN IMAGE INTEGRATING FUNCTIONAL, PHYSIOLOGICAL AND ANATOMICAL IMAGES

CROSS REFERENCE TO RELATED APPLICATION

This application claims priority to U.S. Provisional Application Ser. No. 61/587,150 filed on Jan. 17, 2012, which is hereby incorporated by this reference in its entirety.

ACKNOWLEDGEMENT

This invention was made with government support under Grant No. RR025008, awarded by the National Institutes of Health. The government has certain rights in the invention.

BACKGROUND

Heart failure remains a major concern in developed countries. About 5.7 million people in the U.S. have heart failure, and it results in about 3000,000 deaths each year. One treatment option for patients with symptomatic heart failure (HF) resulting from systolic dysfunction is cardiac resynchronization therapy (CRT). CRT is achieved by simultaneously pacing both the left and right ventricles in a synchronized manner. Numerous clinical investigations have demonstrated that CRT may improve clinical status, functional capacity, and survival in select patients with ventricular dyssynchrony.

Despite the success of cardiac resynchronization therapy shown in several international, multicenter, placebo controlled clinical trials, one out of three patients undergoing CRT will not positively respond to the therapy. Two potential reasons for a patient's non-response to CRT are: 1) poor selection criteria or 2) non-optimal implementation/application of the biventricular pacing device. A significant amount of work has been done to use imaging to address selection of candidates for CRT. However, much less has been done to optimize device performance by selecting and planning lead positions on the myocardium. To achieve the highest physiological and mechanical efficiency and maximize the benefit of CRT, one would like to place the left ventricular (LV) pacing lead at the location of the most delayed contraction that is not predominately scar tissue. Retrospective studies have shown that if the LV lead is located at the "most dyssynchronous" or "latest contracting" region, response rates are improved.

SUMMARY

However, it has been difficult to implement this strategy in a prospective fashion to guide LV lead placement because preoperative imaging does not routinely provide information about coronary venous anatomy and scar burden with respect to the area of latest delayed contraction. Thus, there is need for planning of optimal lead placement location before the CRT procedure.

This disclosure relates to systems, methods, and computer readable storage mediums storing instructions for generating an image that includes functional, physiological and anatomical images of a heart of a patient, and an integrated image. In some embodiments, the generated image may include images of contraction timing, myocardial scar distribution, and coronary vein anatomy. The image may indicate at least one optimal lead location. The contraction timing may be LV contraction timing. The optimal lead location may be the region of latest contraction that is not in an area of significant scar. Thus, the systems, methods and computer-readable storage mediums according to embodiments may improve patient response rate to CRT.

In some embodiments, the generated image may be an integrated image map. In some embodiments, the generated image may include at least one of the anatomical and physiological images mapped to the functional image. The generated image may include a functional image on which the anatomical and physiological images overlap. The anatomical image may include cardiac anatomy, such as coronary vein images. The physiological image may include regions of myocardial scar, such as regions that have suffered a previous heart attack. The functional image may include contraction timing. The functional image may include a contraction timing map that identifies areas of dyssynchrony.

In some embodiments, a method may include: processing a plurality of sets of image data of a heart, each set of image data being different; and generating an image of the heart including functional, anatomical, and physiological images. The method may also include receiving image data.

In some embodiments, the image data may include magnetic resonance (MR) image data. The image data may include a plurality of images acquired from a magnetic resonance imaging (MRI) scan. The image data may be in a Digital Imaging and Communications in Medicine (DICOM) format. The image data may include a header and image data. The header may include image information. The image information may include information regarding the scan. The image information may include but is not limited to number of frames, dimensions of the image, data resolution, and image size.

In some embodiments, the image data may include more than one set of image data. In some embodiments, the image data may include at least two sets of image data. In some embodiments, the image data may include cine image data and contrast image data. The contrast image data may include whole-heart vascular image data acquired during contrast administration and post-contrast image data of muscle of the heart.

In some embodiments, the functional image may be generated from the cine image data. The anatomical and physiological images may be generated from the post-contrast image data. The image data may be acquired from cine MRI. The post-contrast image data may be acquired from a contrast-enhanced sequence. The cine image data may include high frame cine image data acquired over a cardiac cycle. The post-contrast image data may be post Gadolinium enhancement image data.

In some embodiments, the image data may include at least two sequences of data. In some embodiments, the sequences may include a steady-state free precession (SSFP) sequence and a contrast-enhanced sequence. The cine image data may be acquired from the SSFP sequence. The contrast-enhanced sequence may be a 3D whole-heart contrast-enhanced sequence.

In some embodiments, the image data may include functional, anatomical, and physiological image data. In other embodiments, the image data may include functional, anatomical, and physiological images.

In some embodiments, the processing the image data may include mapping the anatomical and physiological images to the functional image.

In some embodiments, the processing the image data may include processing the image data to generate the functional, anatomical and physiological images. In some embodiments, the processing the image data may further include processing a first portion of the image data to generate the functional images. The first portion of the image data may include the cine image data. The processing to generate the functional images may include identifying borders of the heart of the patient at time points and locations in the heart. The borders may be between heart muscle (myocardium) and blood pool of the heart of the patient. The processing may further include determining movement of the borders as a function of time for each location in the heart. The time may be the peak of the motion. The determining may be based on a cross-correlation delay. The processing may further include generating a timing map that identifies areas of dyssynchrony. The timing map may be an AHA 17-segment map on which time is plotted.

In some embodiments, the processing the image data may further include processing a second portion of the image data to generate the anatomical image. The second portion may include the data acquired from a contrast-enhanced sequence. The data may include a plurality of images. The images may include coronary vein images. The processing to generate the anatomical image may include identifying anatomy of the heart on the images. The anatomy may include coronary veins. The identifying may include identifying a position of each vein on the heart on the images. In some embodiments, the processing may include reconstructing the coronary veins in a 3D space. The method may further include mapping the position of each coronary vein to the functional image or dyssynchrony map.

In some embodiments, the processing the image data may further include processing a third portion of the image data to generate the physiological image. The third portion may include the data acquired from a contrast-enhanced administration. The third portion may include post-contrast image data. The data may include a plurality of images. The images may include images of cardiac muscle of the patient. The processing to generate the physiological image may include identifying regions of the cardiac muscle. The regions may be brighter than other regions of the cardiac muscle. The regions may correspond to scar tissue or regions that have suffered a previous myocardial infarction or heart attack. The method may further include mapping the position of each myocardial infarction to the functional image or dyssynchrony map.

In some embodiments, the generated image may include markers identifying locations of optimal lead placement. The generated image may be color-coded. The generated image may include at least one location of optimal lead placement. In some embodiments, the generated image may include three locations of optimal lead placement. Optimal lead placement may correspond to locations that AHA segment that has latest contraction that does not contain a transmural scar.

In some embodiments, the method may further include displaying the generated image. The method may further include transmitting the generated image to an interventional system. The method may further include displaying a position of an interventional device within the heart on the generated image.

In some embodiments, a method may include processing physiological, anatomical, and functional images; and generating an image that includes the physiological, anatomical and functional images. The integrated image may be based on the functional image onto which the physiological and anatomical images are mapped. The generated image may include a functional image on which the anatomical and physiological images overlap. The anatomical images may include cardiac anatomy, such as vein images. The physiological images may include regions of myocardial scar, such as regions that have suffered a previous heart attack. The functional image may include a timing map that identifies areas of dyssynchrony.

In some embodiments, a computer-readable storage medium storing instructions for generating an image that includes functional, physiological and anatomical images, the instructions may include receiving image data; processing the image data; and generating an image including the functional, anatomical, and physiological images. In other embodiments, the instructions may include receiving functional, anatomical, and physiological images; and generating an integrated image including the functional, anatomical, and physiological images.

In some embodiments, a system for generating an integrated image may include an apparatus that includes at least one processor and at least one memory including computer code. The at least one memory and the computer program code configured to, with the at least one processor, may cause the apparatus to perform at least the following: receiving image data; processing the image data; and generating an image including functional, anatomical, and physiological images.

In some embodiments, a generated image may include physiological, anatomical, and functional images. The generated image may be based on the functional image. The generated image may be based on the functional image onto which the physiological and anatomical images are mapped.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DETAILED DESCRIPTION OF THE EMBODIMENTS

Figure 1:
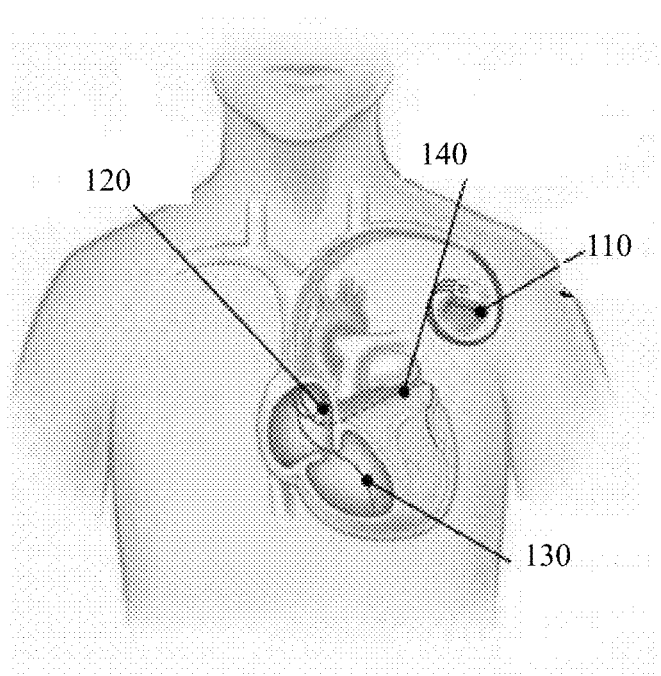
FIG. 1 illustrates an example of a CRT device implanted in a heart of a patient.

The following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The disclosure relates to systems, computer-readable storage mediums, and methods for generating an image that includes functional, anatomical, and physiological images. The generated image may be an image capable of being displayed as a single unified display of the timing of the regional contraction, regional scar, and images of the coronary veins. In some embodiments, the generated image may be an integrated map including the functional, anatomical, and physiological images.

The generated image is described with respect to planning of an optimal lead placement location before a CRT procedure, such as an implantation of a CRT pacing device (e.g., a biventricular pacemaker or a combination of a CRT and implantable cardiac defibrillator (ICD) device). An example of a CRT device implanted in a heart of a patient is shown in FIG. 1. As shown in FIG. 1, a CRT device 100 may include a pulse generator 110 that houses a battery and a computer connected to leads. The CRT device may include 2-3 leads positioned in the right atrium, right ventricle and left ventricle (via the coronary sinus vein). The device 100 shown in FIG. 1 includes leads 120, 130, 140 positioned in the right atrium, right ventricle and left ventricle, respectively. However, it should be understood that the disclosure is not limited to preplanning a CRT procedure and may be used other purposes. For example, the disclosure may be used in other medical intervention procedures planning, such as, for example, atrial fibrillation procedure planning, or atrial flutter procedure planning.

As used herein, optimal lead placement may be the location of the most delayed contraction that is not predominately or does not contain scar tissue (an area of a previous heart attack). Optimal lead placement may also be referred to as "most dyssynchronous" or "latest contracting" region or location.

Methods & Generated Images

The methods of the disclosure are not limited to the steps described herein. The steps may be individually modified or omitted, as well as additional steps may be added.

Unless stated otherwise as apparent from the following discussion, it will be appreciated that terms such as "identifying," "receiving," "integrating," "filtering," "combining," "reconstructing," "segmenting," "generating," "registering," "determining," "obtaining," "processing," "computing," "selecting," "estimating," "detecting," "tracking," or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods may be compiled for execution on a variety of hardware platforms and for interface to a variety of operating systems. In addition, embodiments are not described with reference to any particular programming language. It will be appreciated that a variety of programming languages may be used to implement embodiments of the disclosure.

Figure 2:
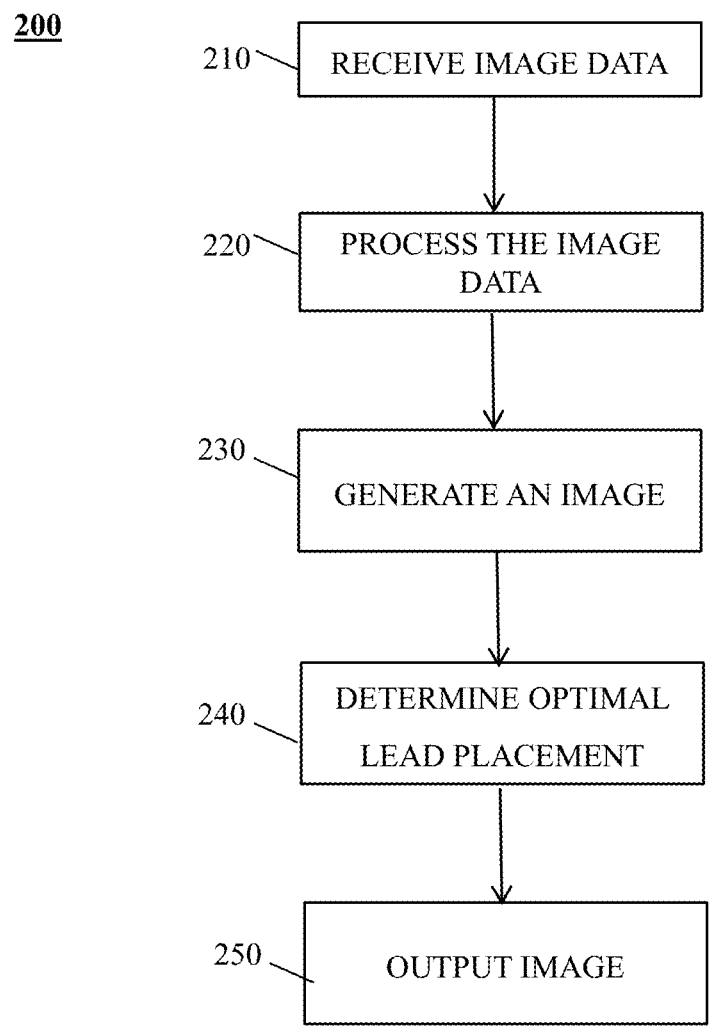
FIG. 2 illustrates a method of generating an image including functional, anatomical, and physiological images, according to embodiments.

FIG. 2 illustrates a method according to embodiments to generate an image including functional, anatomical, and physiological images of a heart of a patient. In some embodiments, a method 200 may include a step 210 of receiving image data. The image data may be of a heart of a patient.

In some embodiments, the image data may include magnetic resonance (MR) image data. The image data may include a plurality of images acquired from a magnetic resonance imaging (MRI) scan. The image data may be in a Digital Imaging and Communications in Medicine (DICOM) format. The image data may include header and image data. The header may include image information. The image information may include information regarding the scan. The image information may include but is not limited to number of frames, dimensions of the image, data resolution, image size, or a combination thereof.

In some embodiments, the image data may include more than one set of image data. In some embodiments, the image data may include at least two sets of image data. In some embodiments, the image data may include at least three sets of different image data. In some embodiments, the image data may include at least cine image data and contrast image data. The contrast image data may include whole-heart vascular image data acquired during contrast administration and post-contrast image data of muscle of the heart.

In some embodiments, the cine image data may be acquired from a steady-state free precession sequence. The post-contrast image data may be acquired from a contrast-enhanced sequence. The cine image data may include high frame cine image data acquired over a cardiac cycle. The post-contrast image data may be post Gadolinium enhancement image data.

In some embodiments, the image data may include at least two sequences of data. In some embodiments, the sequences may include a steady-state free precession (SSFP) sequence and a contrast-enhanced sequence. The cine image data may be acquired from the SSFP sequence. In some embodiments, the cine image data may be acquired in short axis orientation using a SSFP sequence and a temporal resolution of 60 frames per cycle. The contours may be re-sampled at 360 equally spaced radial spokes per slice. The contrast-enhanced sequence may be a 3D whole-heart contrast-enhanced sequence.

In other embodiments, the image data may include at least one of functional, physiological, and anatomical images of a heart of a patient. The functional image may be an image that includes contraction timing. The functional image may be a dyssynchrony map. In some embodiments, the physiological image may be an image that includes regional scar distribution. The physiological image may be a map. The anatomical image may be an image that includes coronary veins of the heart.

In some embodiments, the method may further include a step 220 of processing the image data. In some embodiments, the processing the image data may include processing the image data to generate functional, physiological and anatomical images. In some embodiments, the functional image may be generated from the cine image data. The anatomical and physiological images may be generated from the post-contrast image data.

In other embodiments, the processing step 220 the image data may be omitted. The receiving step 210 may include receiving functional, physiological and anatomical images. It should also be understood that the processing steps may be performed in any order and are not limited to the order discussed below.

In some embodiments, the processing step 220 the image data may further include processing a first portion of the image data or a first set of image data to generate the functional image. In some embodiments, the first portion or first set may include the cine image data. The functional image may be based on a stack of cine images.

In some embodiments, the functional image may be a dyssynchrony map. In some embodiments, the distance of the points on the contours from the center of mass of the LV may provide radial displacement curves for each of the 360 points along the contour of each slice. In some embodiments, the functional image may be generated automatically. In other embodiments, the generation of the functional image may include manual steps.

In some embodiments, processing to generate the functional image may include identifying borders of the heart on each image. The borders may be between the myocardium and the blood pool over the time points and all locations in the heart. The movement of these borders may be determined as a function of time for each location in the heart. The time of the peak of the motion may be identified with a mathematical function (e.g., a cross-correlation delay) and the time may be plotted on a map (AHA 17-segment map). The map may be a timing map that identifies areas of dyssynchrony (also referred to as a dyssynchrony map).

Figure 4:
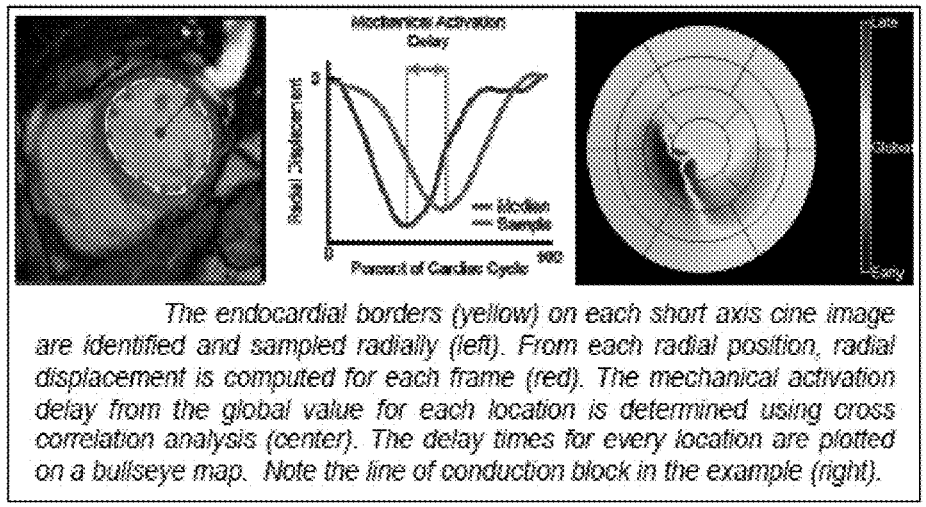
FIG. 4 illustrates an example of processing image data to generate a functional image.

FIG. 4 show an example of the processing of the image data to generate a functional image. The borders may include endocardial borders. Each of the borders may be sampled radially, as shown in the left image of FIG. 4. From each radial position, radial displacement may be computed. In some embodiments, the mechanical activation delay from each the global value for each location may be determined using a cross-correlation analysis, as shown in the center image of FIG. 4. Next, the delay times for each location may be plotted on a bullseye map, as shown in the right image of FIG. 4. Each of these steps may be performed automatically and/or manually.

In some embodiments, the processing step may further include processing a second portion of the image data or second set of image data to generate an anatomical image. In some embodiments, the second portion or second set may include the data acquired from the contrast-enhanced sequence. In some embodiments, the contrast may be a gadolinium contrast agent. The contrast-enhanced sequence may be a 3D whole-heart contrast-enhanced sequence. In some embodiments, the data may be acquired using an imaging protocol in which a 3D whole-heart contrast-enhanced sequence during which a 0.2 mmol/kg of a gadolinium contrast agent is infused at 0.03 cc/sec to produce a long plateau of maximum contrast agent concentration in the blood and allow for more k-space data to be acquired during maximum contrast concentration. The data may include a plurality of images. The images may include coronary vein images and the anatomy may be coronary veins.

In some embodiments, the processing to generate the anatomical image may include identifying anatomy of the heart on the images. The identifying may include identifying a position of coronary vein on the heart on each of the images. In some embodiments, the processing may include reconstructing the coronary veins in a 3D space.

In some embodiments, the step 220 of processing the image data may further include processing a third portion of the image data or third set of image data to generate the physiological image. The physiological image may be an image or map of regional scar distribution. The map may be the same type of map as the functional image. The third portion or set may include the data acquired from a contrast-enhanced administration. The third portion or set may include post-contrast image data. The data may include a plurality of images. The images may include images of cardiac muscle of the patient. The physiological image may be based on echo images. In some embodiments, the echo image may be inversion recovery prepared, segmented, and gradient echo images.

In some embodiments, the processing to generate the physiological image may include identifying regions of the cardiac muscle. The regions may be brighter than other regions of the cardiac muscle. The regions may correspond to scar tissue or regions that have suffered a previous myocardial infarction or heart attack. In some embodiments, the regions of the cardiac muscle may include the endocardial, epicardial and infarct borders of the heart.

In some embodiments, based on the borders, the transmularity of infarct may be determined. In some embodiments, from the identified borders, radial spokes may be drawn through the myocardium from the center of the mass outward. The transmularity of infarct along each spoke may be determined by the thickness of the infarct divided by the total endocardial-to-epicardial distance. In some embodiments, 360° spokes may be used to display transmularity within each given slice. Each of these steps may be performed automatically and/or manually.

In some embodiments, the method may further include a step of 230 of generating at least one image that includes functional, physiological and anatomical images. In some embodiments, the generated image may include images of LV contraction timing, myocardial scar distribution, and coronary vein anatomy. The generated image may indicate at least one optimal lead location. The optimal lead location may be the region of latest contraction that is not in an area of significant scar.

In some embodiments, the generated image may be an integrated image map. In some embodiments, the generated image may include the anatomical and physiological images mapped to the functional image. The generated image may include a functional image on which the anatomical and physiological images overlap. The anatomical images may include cardiac anatomy, such as vein images. The physiological images may include regions of myocardial scar, such as regions that have suffered a previous heart attack. The functional image may include a timing map that identifies areas of dyssynchrony.

Figure 3:
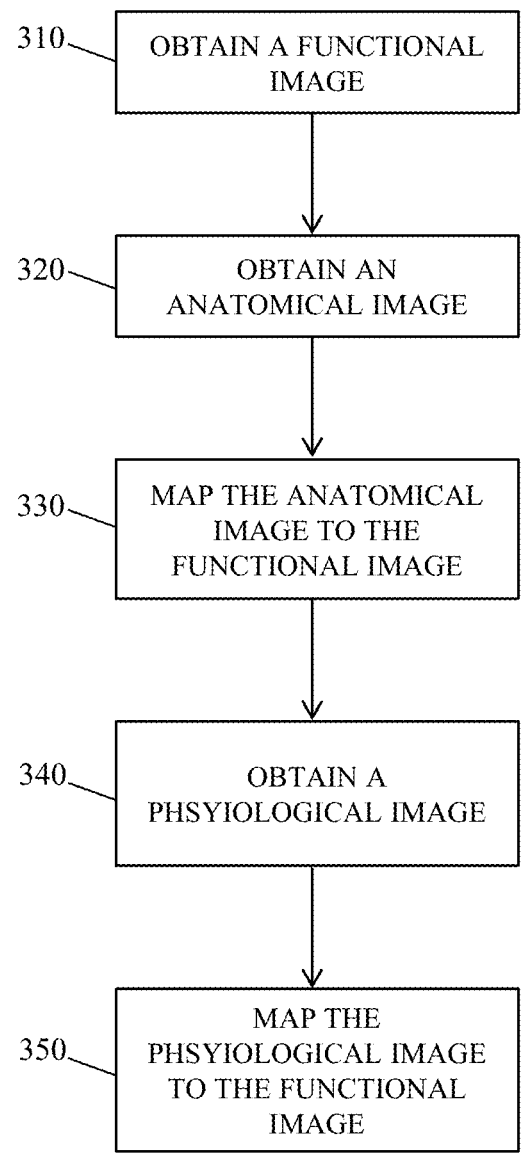
FIG. 3 illustrates steps of generating the image according to embodiments.

FIG. 3 illustrates steps to generate an image including functional, physiological, and anatomical images. In some embodiments, the steps of generating an image may occur sequentially after each type of image is received and/or processed. In some embodiments, the steps 310, 320, and 340 of obtaining images may include only receiving the image. In other embodiments, the steps 310, 320, and 340 of obtaining may further include other steps. In some embodiments, the steps 310, 320 and 340 may occur after each and/or all of the images are processed.

It should be also understood that the steps of generating are not limited to the order illustrated in FIG. 3 and may occur in a different order. For example, the images may be received and mapped in any order. The steps of generating may occur simultaneously, sequentially, or combination thereof. The steps of generating may also occur simultaneously, sequentially, or combination thereof with other steps of the disclosure.

In some embodiments, the step 300 of generating the image may include the step of 310 of obtaining the functional image and step of 320 of obtaining the anatomical image. The images may be obtained, for example, by generating functional and anatomical images as discussed above and/or receiving generated images. The step 300 of generating the image may further include a step 330 of mapping the anatomical image to the functional image.

In some embodiments, the step 300 may further include a step 340 of obtaining a physiological image and a step 350 of mapping the physiological image to the functional image. The images may be obtained, for example, by generating functional and anatomical images as discussed above and/or receiving generated images.

Figure 5:
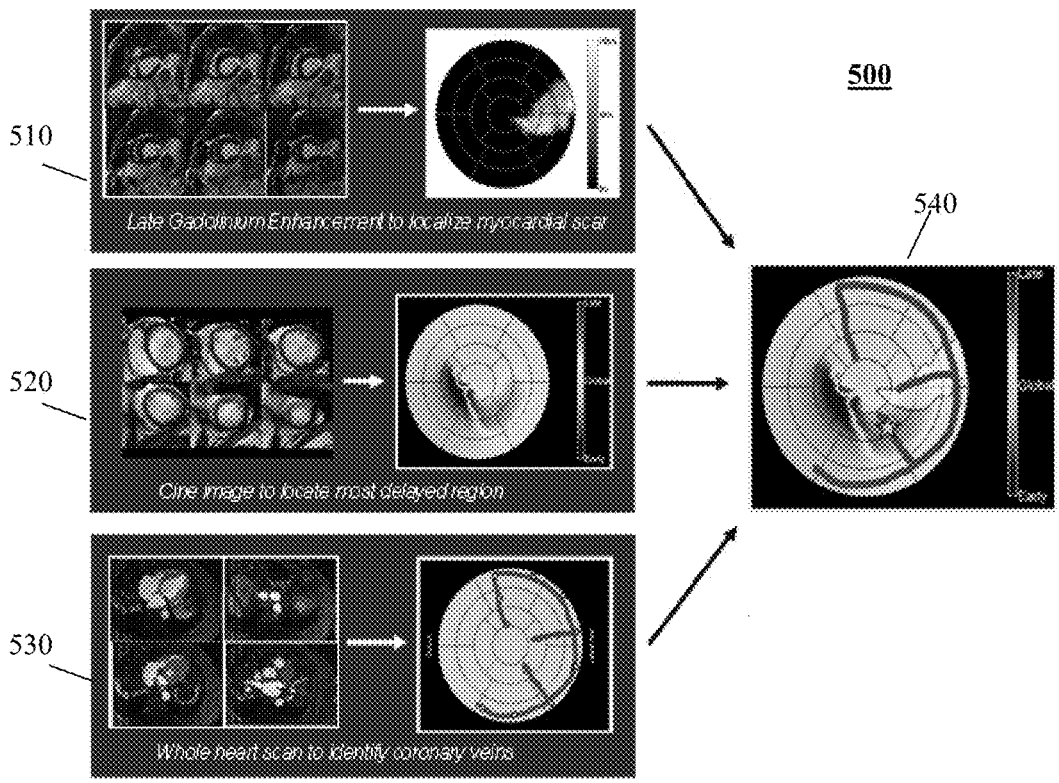
FIG. 5 illustrates an example of processing image data to generate an image including functional, anatomical, and physiological images, according to embodiments.

An example of a generated image map may be found in FIG. 5. As shown in FIG. 5, an image 540 may be generated based on a physiological image 510, a functional image 520, and an anatomical image 530. The image 540 may be a dyssynchrony map onto which the physiological image 510 and the anatomical image 530 are mapped.

In some embodiments, the method 200 may include a step 240 of determining at least one location of optimal lead placement. In some embodiments, the step 240 may occur before, during, and or after the step 230. The step 240 may determine at least one region of latest contraction(s) that is not in an area of significant scar.

In some embodiments, more than one location of optimal lead placement may be determined. Any number of locations may be determined. In some embodiments, the determining may include identifying the at least one location of optimal lead placement on the generated image.

In some embodiments, the generated image may indicate at least one location of optimal lead placement. In some embodiments, the generated image may include more than one location of optimal lead placement. The generated image may include any number of optimal lead placements. In some embodiments, the generated image may include at least three locations of optimal lead placement.

In some embodiments, the generated image may include at least one marker identifying each location of optimal lead placement. The marker may be any symbol. As shown in FIG. 5, the marker may be a star. In some embodiments, the generated image and/or at least one optimal lead image may be color-coded.

In some embodiments, the generated image may further include a position of an interventional device within the heart. The interventional device may be, for example, any device used for cardiac intervention procedures. The interventional device may include but is not limited to a probe, a catheter, and an ablation device.

In some embodiments, the method 200 may further include a step 250 of outputting the image. In some embodiments, the outputting may include printing the generated image. In other embodiments, the outputting may include storing the generated image.

In some embodiments, the outputting may include displaying the generated image. In some embodiments, the method may further include displaying at least one parameter related to a region or location of the generated image. The parameter may relate to anatomical, functional, and/or physiological features of the heart. The parameter may include but is not limited to diameter of the coronary sinus, the path length of the coronary sinus, the viewing of the significant branches of the coronary sinus, the quantification of the curvature, and the quantification of the degree of obstruction, the degree of transmularity, and the contraction time. The region may be selected by the operator or may be displayed based on a position of an interventional device.

In some embodiments, the outputting may further include transmitting the generated image to another system. In some embodiments, the method may further include transmitting the generated image to an interventional system. The interventional system may be any known system configured for cardiac intervention procedures. The method may further include determining a position of an interventional device of a heart with respect to the image, displaying a position of an interventional device within the heart on the generated image, or a combination thereof. The method may further include displaying specific parameters of a selected region of the heart.

In some embodiments, the generated image may be used for planning a cardiac interventional procedure, such as implanting a CRT device.

System Implementation

Figure 6:
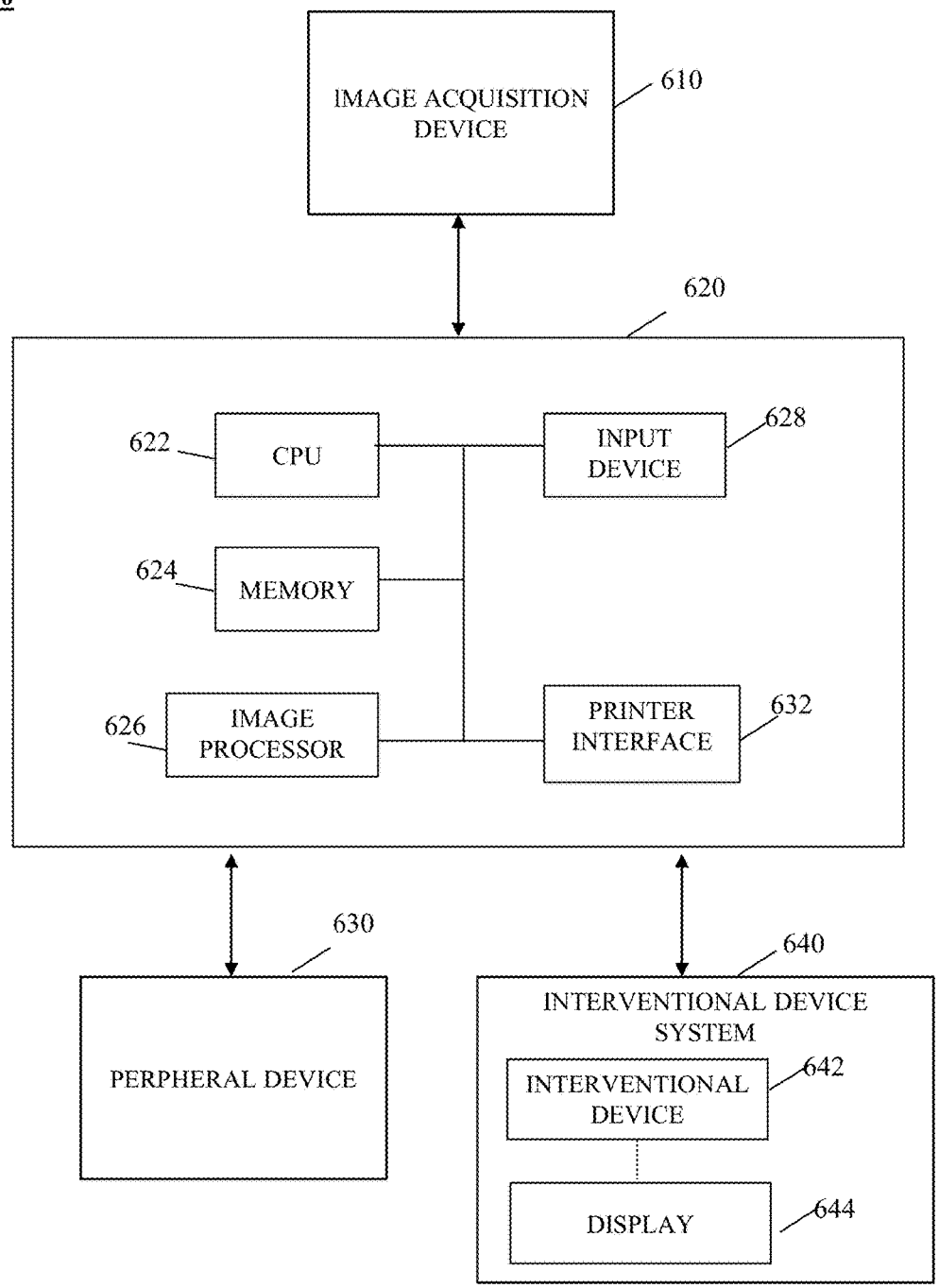
FIG. 6 shows an example of a system according to embodiments.

FIG. 6 shows an example of a system 600 that may be used to generate an integrated image according to embodiments. The system 600 may include any number of modules that communicate with other through electrical or data connections (not shown). In some embodiments, the modules may be connected via a wired network, wireless network, or combination thereof. In some embodiments, the networks may be encrypted. In some embodiments, the wired network may be, but is not limited to, a local area network, such as Ethernet, or wide area network. In some embodiments, the wireless network may be, but is not limited to, any one of a wireless wide area network, a wireless local area network, a Bluetooth network, a radio frequency network, or another similarly functioning wireless network.

Although the modules of the system are shown as being directly connected, the modules may be indirectly connected to one or more of the other modules of the system. In some embodiments, a module may be only directly connected to one or more of the other modules of the system.

It is also to be understood that the system may omit any of the modules illustrated and/or may include additional modules not shown. It is also be understood that more than one module may be part of the system although one of each module is illustrated in the system. It is further to be understood that each of the plurality of modules may be different or may be the same. It is also to be understood that the modules may omit any of the components illustrated and/or may include additional component(s) not shown.

In some embodiments, the modules provided within the system may be time synchronized. In further embodiments, the system may be time synchronized with other systems, such as those systems that may be on the medical facility network.

The system 600 may include an image acquisition device 610 configured to acquire the image data of a patient. The image acquisition device 610 may be any device configured to acquire images from a magnetic resonance imaging (MRI) scan.

The system 600 may further include a computer system 620 to carry out the image processing and generating. The computer system 620 may further be used to control the operation of the system or a computer separate system may be included.

The computer system 620 may also be connected to another computer system as well as a wired or wireless network. The computer system 620 may receive or obtain the image data from the image acquisition device 610 or from another module, such as a hospital server provided on a network.

The computer system 620 may include a number of modules that communicate with each other through electrical and/or data connections (not shown). Data connections may be direct wired links or may be fiber optic connections or wireless communications links or the like. The computer system 620 may also be connected to permanent or back-up memory storage, a network, or may communicate with a separate system control through a link (not shown). The modules may include a CPU 622, a memory 624, an image processor 626, an input device 628, and a printer interface 632.

The CPU 622 may any known central processing unit, a processor, or a microprocessor. The CPU 622 may be coupled directly or indirectly to memory elements. The memory 624 may include random access memory (RAM), read only memory (ROM), disk drive, tape drive, etc., or a combinations thereof. The memory may also include a frame buffer for storing image data arrays.

The present disclosure may be implemented as a routine that is stored in memory 624 and executed by the CPU 622. As such, the computer system 620 may be a general purpose computer system that becomes a specific purpose computer system when executing the routine of the disclosure.

The computer system 620 may also include an operating system and micro instruction code. The various processes and functions described herein may either be part of the micro instruction code or part of the application program or routine (or combination thereof) that is executed via the operating system. In addition, various other peripheral devices 630 may be connected to the computer platform such as an additional data storage device, a printing device, and I/O devices.

The image processor 626 may be any known central processing unit, a processor, or a microprocessor. In some embodiments, the image processor also processes the data. In other embodiments, the image processor 626 may be replaced by image processing functionality on the CPU 622.

The input device 628 may include a mouse, joystick, keyboard, track ball, touch activated screen, light wand, voice control, or any similar or equivalent input device, and may be used for interactive geometry prescription. The input device 628 may control the peripheral device 630.

The peripheral device 630 may include but is not limited to a display, printer device, storage device, as well as other I/O devices. The display and the printer may be any known display screen and any known printer, respectively, either locally or network connected. In some embodiments, the input device 628 may control the production and display of images on a display, and printing of the images via the printer interface 632.

In some embodiments, the image processor 626 may be configured to transform the data (through Fourier transformation or another technique) from the image acquisition device 610 into image data. In some embodiments, the image processor 626 may be configured to process the image data to generate the functional, physiological, and anatomical images. The image data may then be stored in the memory 624. In other embodiments, another computer system may assume the image reconstruction or other functions of the image processor 626. In response to commands received from the input device 628, the image data stored in the memory 624 may be archived in long term storage or may be further processed by the image processor 626 and presented on the display 630.

In some embodiments, the system 600 may include at least one interventional device system 640. The interventional device system 640 may at least include an interventional device 644. The interventional device may include any device used for cardiac intervention procedures. The interventional device may include but is not limited to a probe, a catheter, and an ablation device. The interventional device system 640 may further include at least a display 644 on which the interventional device 642 may be displayed on the generated image. The interventional device system 640 may also include a computer system like computer system 620.

It is to be understood that the embodiments of the disclosure be implemented in various forms of hardware, software, firmware, special purpose processes, or a combination thereof. In one embodiment, the disclosure may be implemented in software as an application program tangible embodied on a computer readable program storage device. The application program may be uploaded to, and executed by, a machine comprising any suitable architecture. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

It is to be further understood that, because some of the constituent system components and method steps depicted in the accompanying figures can be implemented in software, the actual connections between the systems components (or the process steps) may differ depending upon the manner in which the disclosure is programmed. Given the teachings of the disclosure provided herein, one of ordinary skill in the related art will be able to contemplate these and similar implementations or configurations of the disclosure.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed is:

1. A method for generating an image including functional, anatomical, and physiological images of a heart of a patient, comprising:

processing a plurality of sets of magnetic resonance (MR) image data of a heart to generate a functional image, an anatomical image, and a physiological image of the heart, the plurality of sets of MR image data including a set of cine image data and one or more sets of contrast-enhanced image data, the functional image being generated from the set of cine image data and being a contraction timing map that includes contraction timing and identifies areas of dyssynchrony, and the physiological image and the anatomical image being generated from the one or more sets of contrast-enhanced image data, the physiological image including regional scar distribution;

generating an integrated image of the heart, the integrated image including functional, anatomical, and physiological images, the integrated image being based on the functional image on which the anatomical and physiological images are mapped;

determining one or more optimal lead placement locations for one or more leads of an implantable device; and identifying the one or more optimal lead placement locations on the integrated image.

2. The method of claim 1, wherein the processing includes:

processing the set of cine image data to generate the functional image;

processing a first set of contrast-enhanced image data to generate the physiological image; and processing a second set of contrast-enhanced image data to generate the anatomical image.

3. The method of claim 1, wherein the anatomical image includes coronary veins.

4. The method of claim 1, wherein:

the functional image is a dyssynchrony map; an the integrated image is an integrated map that includes the functional, anatomical, and physiological images, and the integrated map is based on the functional image on which the anatomical and physiological images overlap.

5. The method of claim 1, further comprising: displaying a position of an interventional device on the integrated image.

6. The method according to claim 1, wherein one or more optimal lead placement locations are determined based on the contraction timing and the scar distribution.

7. The method according to claim 6, wherein each optimal lead placement location corresponds to a region of latest contraction that is not an area of significant scar.

8. The method according to claim 1, further comprising: displaying the integrated image, wherein each of the one or more optimal lead placement locations is identified on the integrated image by a marker.

9. The method according to claim 1, wherein the contraction timing is of a left ventricle (LV) of the heart.

10. The method according to claim 1, wherein the processing the cine image data to generate the functional image includes determining movement of borders of the heart as a function of time for each location in the heart.

11. The method according to claim 10, wherein the borders include endocardial borders of the heart.

12. The method according to claim 1, wherein:

the anatomical image includes anatomy of the heart, and the anatomy of the heart includes coronary veins, and the mapping the anatomical image to the functional image includes mapping a position of each coronary vein to the functional image.

13. A non-transitory computer-readable storage medium storing instructions for generating functional, physiological and anatomical images of a heart of a patient, the instructions comprising:

processing a plurality of sets of magnetic resonance (MR) image data of a heart to generate a functional image, an anatomical image, and a physiological image of the heart, the plurality of sets of MR image data including a set of cine image data and one or more sets of contrast-enhanced image data, the functional image being generated from the set of cine image data and being a contraction timing map that includes contraction timing and identifies areas of dyssynchrony, and the physiological image and the anatomical image being generated from the one or more sets of contrast-enhanced image data, the physiological image including regional scar distribution;

generating an integrated image of a heart, the integrated image including the functional, anatomical, and physiological images, the integrated image being based on the functional image on which the anatomical and physiological images are mapped;

determining one or more optimal lead placement locations for one or more leads of an implantable device; and identifying the one or more optimal lead placement locations on the integrated image.

14. The non-transitory computer-readable storage medium of claim 13, wherein the anatomical image includes coronary veins.

15. The non-transitory computer-readable storage medium of claim 13, wherein one or more optimal lead placement locations are determined based on the contraction timing and the scar distribution.

16. The non-transitory computer-readable storage medium of claim 15, wherein each optimal lead placement location corresponds to a region of latest contraction that is not an area of significant scar.

17. The non-transitory computer-readable storage medium of claim 13, further comprising:

displaying the integrated image, wherein each of the one or more optimal lead placement locations is identified on the integrated image by a marker.

18. The non-transitory computer-readable storage medium of claim 13, wherein the contraction timing is of a left ventricle (LV) of the heart.

19. The non-transitory computer-readable storage medium of claim 13, wherein the processing the cine image data to generate the functional image includes determining movement of borders of the heart as a function of time for each location in the heart.

20. The non-transitory computer-readable storage medium of claim 13, wherein:

the anatomical image includes anatomy of the heart, and the anatomy of the heart includes coronary veins, and the mapping the anatomical image to the functional image includes mapping a position of each coronary vein to the functional image.

* * * * *